United States Patent
Kobayashi et al.

(10) Patent No.: US 9,968,318 B2
(45) Date of Patent: May 15, 2018

(54) ESTIMATING APPARATUS, X-RAY DIAGNOSIS APPARATUS, AND ESTIMATING METHOD

(71) Applicant: Toshiba Medical Systems Corporation, Otawara-shi (JP)

(72) Inventors: Tadaharu Kobayashi, Otawara (JP); Manabu Tanaka, Otawara (JP); Teruomi Gunji, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 358 days.

(21) Appl. No.: 14/803,484

(22) Filed: Jul. 20, 2015

(65) Prior Publication Data
US 2015/0320381 A1    Nov. 12, 2015

Related U.S. Application Data

(63) Continuation of application No. PCT/JP2014/051145, filed on Jan. 21, 2014.

(30) Foreign Application Priority Data

Jan. 22, 2013   (JP) .................................. 2013-009411
Jan. 21, 2014   (JP) .................................. 2014-008948

(51) Int. Cl.
*A61B 6/00* (2006.01)
*A61B 6/03* (2006.01)

(52) U.S. Cl.
CPC ............... *A61B 6/463* (2013.01); *A61B 6/03* (2013.01); *A61B 6/542* (2013.01); *A61B 6/583* (2013.01);

(Continued)

(58) Field of Classification Search
None
See application file for complete search history.

(56) References Cited

U.S. PATENT DOCUMENTS

2010/0290591 A1*  11/2010  Spahn ..................... A61B 6/08
                                                        378/98.5

FOREIGN PATENT DOCUMENTS

JP    2000-152924 A    6/2000
JP    2007-089923 A    4/2007
(Continued)

OTHER PUBLICATIONS

International Search Report dated Mar. 25, 2014 for PCT/JP2014/051145 filed on Jan. 21, 2014 with English Translation.

(Continued)

*Primary Examiner* — Hoon Song
(74) *Attorney, Agent, or Firm* — Oblon, McClelland, Maier & Neustadt, L.L.P.

(57) ABSTRACT

An estimating apparatus according to an embodiment includes specifying circuitry, deriving circuitry, and display control circuitry. The specifying circuitry specifies a region of a subject irradiated with X-rays emitted from an X-ray tube of an X-ray CT apparatus on a human body model schematically representing the subject. The deriving circuitry assumes the human body model to be at a position where the subject is arranged in radiography performed by the X-ray CT apparatus and derives an exposure dose of the X-rays on a surface of the region specified by the specifying circuitry on the human body model based on irradiation conditions in the radiography. The display control circuitry displays, on a display, information in which the exposure dose derived by the deriving circuitry is associated with the region on the human body model specified by the specifying circuitry.

14 Claims, 9 Drawing Sheets

(52) U.S. Cl.
CPC ............... *A61B 6/032* (2013.01); *A61B 6/465* (2013.01); *A61B 6/503* (2013.01); *A61B 6/504* (2013.01)

(56) References Cited

FOREIGN PATENT DOCUMENTS

| | | |
|---|---|---|
| JP | 2007-175323 A | 7/2007 |
| JP | 2010-068978 A | 4/2010 |

OTHER PUBLICATIONS

International Written Opinion dated Mar. 25, 2014 for PCT/JP2014/051145 filed on Jan. 21, 2014.

\* cited by examiner

FIG.4

| FOV | kV | mA | ACTUAL MEASUREMENT VALUE ID |
|---|---|---|---|
| 500 | 220 | I1<br>I2<br>...<br>In | 0001-1<br>0001-2<br>...<br>0001-n |
| 500 | 150 | I1<br>I2<br>...<br>In | 0002-1<br>0002-2<br>...<br>0002-n |
| 500 | 80 | I1<br>I2<br>...<br>In | 0003-1<br>0003-2<br>...<br>0003-n |
| 320 | 220 | I1<br>I2<br>...<br>In | 0004-1<br>0004-2<br>...<br>0004-n |
| 320 | 150 | I1<br>I2<br>...<br>In | 0005-1<br>0005-2<br>...<br>0005-n |
| 320 | 80 | I1<br>I2<br>...<br>In | 0006-1<br>0006-2<br>...<br>0006-n |
| 240 | 220 | I1<br>I2<br>...<br>In | 0007-1<br>0007-2<br>...<br>0007-n |
| 240 | 150 | I1<br>I2<br>...<br>In | 0008-1<br>0008-2<br>...<br>0008-n |
| 240 | 80 | I1<br>I2<br>...<br>In | 0009-1<br>0009-2<br>...<br>0009-n |
| 180 | 220 | I1<br>I2<br>...<br>In | 0010-1<br>0010-2<br>...<br>0010-n |
| 180 | 150 | I1<br>I2<br>...<br>In | 0011-1<br>0011-2<br>...<br>0011-n |
| 180 | 80 | I1<br>I2<br>...<br>In | 0012-1<br>0012-2<br>...<br>0012-n |
| 120 | 220 | I1<br>I2<br>...<br>In | 0013-1<br>0013-2<br>...<br>0013-n |
| 120 | 150 | I1<br>I2<br>...<br>In | 0014-1<br>0014-2<br>...<br>0014-n |
| 120 | 80 | I1<br>I2<br>...<br>In | 0015-1<br>0015-2<br>...<br>0015-n |

ESTIMATING APPARATUS, X-RAY DIAGNOSIS APPARATUS, AND ESTIMATING METHOD

CROSS-REFERENCE TO RELATED APPLICATIONS

This application is a continuation of PCT international application Ser. No. PCT/JP2014/051145 filed on Jan. 21, 2014 which designates the United States, incorporated herein by reference, and which claims the benefit of priority from Japanese Patent Application No. 2013-009411, filed on Jan. 22, 2013 and Japanese Patent Application No. 2014-008948, filed on Jan. 21, 2014, the entire contents of which are incorporated herein by reference.

FIELD

Embodiments described herein relate generally to an estimating apparatus, an x-ray diagnosis apparatus, and an estimating program.

BACKGROUND

There have been developed dose management systems that manage an X-ray dose delivered to the surface of a subject as a skin exposure dose in radiography of an X-ray image performed by an X-ray diagnosis apparatus. Dose management systems, for example, calculate an exposure dose of the subject from irradiation conditions of the X-ray diagnosis apparatus. Dose management systems generate a simulated human body model based on body information of the subject and display the exposure dose in association with the human body model on a monitor.

Recently, some computed tomography (CT) inspections with an X-ray CT apparatus may be performed in combination with treatment with an X-ray diagnosis apparatus. An operating person (hereinafter, referred to as an "operator"), such as a doctor, performs intravascular treatment in a manner supported by an X-ray diagnosis apparatus after making a diagnosis with an X-ray CT apparatus.

BRIEF DESCRIPTION OF THE DRAWINGS

FIG. 4 is a diagram of an example of a data structure stored in actual measurement value storage circuitry;

DETAILED DESCRIPTION

An estimating apparatus according to an embodiment includes specifying circuitry, deriving circuitry, and display control circuitry. The specifying circuitry specifies a region of a subject irradiated with X-rays emitted from an X-ray tube of an X-ray CT apparatus on a human body model schematically representing the subject. The deriving circuitry assumes the human body model to be at a position where the subject is arranged in radiography performed by the X-ray CT apparatus and derives an exposure dose of the X-rays on a surface of the region specified by the specifying circuitry on the human body model based on irradiation conditions in the radiography. The display control circuitry displays, on a display, information in which the exposure dose derived by the deriving circuitry is associated with the region on the human body model specified by the specifying circuitry.

An estimating apparatus, an x-ray diagnosis apparatus, and an estimating program according to embodiments are described below with reference to the accompanying drawings.

First Embodiment

Figure 1:
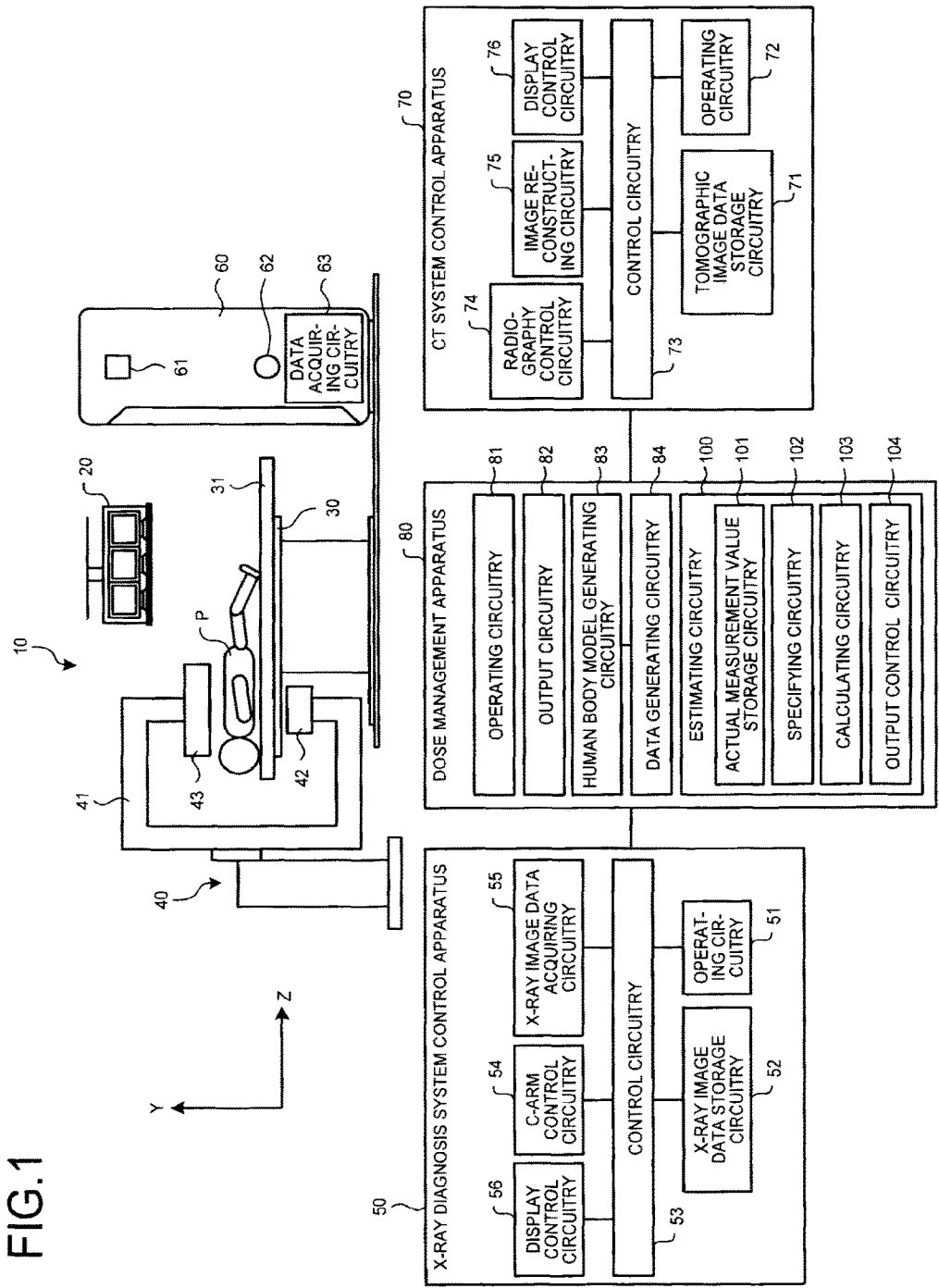
FIG. 1 is a diagram of an exemplary configuration of a cardiovascular X-ray diagnosis system according to a first embodiment.

The following describes a first embodiment using a cardiovascular X-ray diagnosis system 10 as an example. FIG. 1 is a diagram of an exemplary configuration of the cardiovascular X-ray diagnosis system 10 according to the first embodiment. The cardiovascular X-ray diagnosis system 10 according to the first embodiment includes a monitor 20, a couch 30, a C-arm holding apparatus 40, an X-ray diagnosis system control apparatus 50, a computed tomography (CT) apparatus gantry 60, a CT system control apparatus 70, and a dose management apparatus 80. A subject P is not included in the cardiovascular X-ray diagnosis system 10. In the following description, the C-arm holding apparatus 40 and the X-ray diagnosis system control apparatus 50 may be collectively referred to as an X-ray diagnosis apparatus 200. The CT apparatus gantry 60 and the CT system control apparatus 70 may be collectively referred to as an X-ray CT apparatus 300.

The cardiovascular X-ray diagnosis system 10 performs a CT inspection with the X-ray CT apparatus 300 in combination with treatment with the X-ray diagnosis apparatus 200. An operating person (hereinafter, referred to as an "operator"), such as a doctor, refers to an X-ray CT image (a tomographic image) resulting from radiography performed by the X-ray CT apparatus 300 to specify a stenosis site in a heart. The operator, for example, performs intravascular intervention with a catheter while referring to an X-ray image (a fluoroscopic image) of the stenosis site resulting from radiography performed by the X-ray diagnosis apparatus 200.

The following describes each unit included in the cardiovascular X-ray diagnosis system 10. The monitor 20 displays an X-ray image, such as a fluoroscopic image, resulting from radiography performed by the X-ray diagnosis apparatus 200 and a tomographic image based on tomographic image data resulting from radiography performed by the X-ray CT apparatus 300, for example. The couch 30 includes a couchtop 31 on which the subject P is placed and can move in the vertical direction and the horizontal direction. The couch 30 can move the couchtop 31 in the longitudinal direction or in both the longitudinal and the short directions. The couch 30 moves the subject P to a radiography area of the X-ray diagnosis apparatus 200 and a radiography area of the X-ray CT apparatus 300 by moving the couch 30 itself and/or the couchtop 31. In the cardiovascular X-ray diagnosis system 10, the couch 30 is shared by the X-ray diagnosis apparatus 200 and the X-ray CT apparatus 300.

The C-arm holding apparatus 40 supports a C-arm 41. The C-arm 41 supports an X-ray tube 42 and an X-ray detector 43 in a manner facing each other. The X-ray tube 42 emits X-rays. The X-ray detector 43 detects X-rays emitted from the X-ray tube 42 and passing through the subject P. The pair of the X-ray tube 42 and the X-ray detector 43 rotates about a geometric rotation center.

The X-ray diagnosis system control apparatus 50 controls the C-arm holding apparatus 40 to acquire X-ray image data of the subject P. The X-ray diagnosis system control apparatus 50 includes operating circuitry 51, X-ray image data storage circuitry 52, control circuitry 53, C-arm control circuitry 54, X-ray image data acquiring circuitry 55, and display control circuitry 56, for example.

The operating circuitry 51 is a control panel, a foot switch, a joystick, or the like and receives input of various operations performed on the X-ray diagnosis apparatus 200 from the operator. The operating circuitry 51 receives, from the operator, an operation performed on the couch 30 to move an observation target in the subject P to the center of a screen, for example. Thus, the control circuitry 53 moves the couch 30 in response to the operation performed by the operator. The operating circuitry 51 receives an operation to rotate the C-arm 41 from the operator. Thus, the C-arm control circuitry 54 rotates the C-arm 41 in response to the operation performed by the operator. The operating circuitry 51 receives a setting of radiography conditions from the operator. The operating circuitry 51, for example, receives an operation to set a coronary artery as an observation target from the operator. The operating circuitry 51 receives information, such as source-isocenter distance (SID) and field of view (FOV), from the operator, for example. The values of SID, FOV, and the like may be held in advance in the X-ray diagnosis apparatus 200. The operating circuitry 51 receives an instruction to acquire X-ray image data from the operator.

The X-ray image data storage circuitry 52 stores therein X-ray image data and the like. The control circuitry 53 collectively controls the X-ray diagnosis system control apparatus 50 based on an instruction received from the operating circuitry 51. The C-arm control circuitry 54 controls rotation and other operations of the C-arm 41 under the control of the X-ray image data acquiring circuitry 55.

If an instruction to acquire X-ray image data is received from the operator through the operating circuitry 51, the X-ray image data acquiring circuitry 55 controls the X-ray tube 42, the X-ray detector 43, and the C-arm control circuitry 54, thereby acquiring X-ray image data. The X-ray image data acquiring circuitry 55 acquires an image of X-rays incident on the subject P and projected onto the X-ray detector 43. The X-ray image data acquiring circuitry 55 transmits the acquired X-ray image data to the display control circuitry 56.

The CT apparatus gantry 60 includes an X-ray tube 61, an X-ray detector 62, and data acquiring circuitry 63. The X-ray tube 61 generates X-rays based on a predetermined tube voltage and tube current applied by high-voltage generating circuitry, which is not illustrated. The X-ray tube 61 emits the X-rays to the subject P placed on the couch 30 while moving and rotating around the subject P. The X-ray detector 62 is supported at a position facing the X-ray tube 61 by a rotatable support and detects an X-ray dose of the X-ray beams passing through the subject P. The X-ray detector 62 is a multiple-array detector composed of a plurality of channels, that is, a plurality of X-ray detecting channels arranged in a two-dimensional matrix, in a plurality of arrays. The data of the detected transmission X-ray dose is output to the data acquiring circuitry 63.

The data acquiring circuitry 63 acquires the data of the transmission X-ray dose detected by the X-ray detector 62. The data acquiring circuitry 63 performs amplification, analog-to-digital (A/D) conversion, and other processing on the data of the acquired transmission X-ray dose and then outputs the data to the CT system control apparatus 70.

The CT system control apparatus 70 includes tomographic image data storage circuitry 71, operating circuitry 72, control circuitry 73, radiography control circuitry 74, image reconstructing circuitry 75, and display control circuitry 76. The tomographic image data storage circuitry 71 stores therein tomographic image data and the like. The operating circuitry 72 receives input from the operator. The operating circuitry 72 is a keyboard or a mouse, for example, and outputs a signal corresponding to input from the operator to the radiography control circuitry 74. The control circuitry 73 collectively controls the CT system control apparatus 70 based on an instruction received from the operating circuitry 72.

The radiography control circuitry 74 controls operations of each circuitry of the CT apparatus gantry 60. The radiography control circuitry 74, for example, controls a rotational operation of the support, an operation of the X-ray tube 61, an operation of the X-ray detector 62, and an operation of the data acquiring circuitry 63 based on an input signal from the operating circuitry 72.

The image reconstructing circuitry 75 performs generation of image data and various kinds of image processing based on the data acquired by the CT apparatus gantry 60. The image reconstructing circuitry 75, for example, reconstructs projection data transmitted from the data acquiring circuitry 63 based on predetermined reconstruction parameters, such as a reconstruction area size, a reconstruction matrix size, and a threshold used to extract a region of interest. Thus, the image reconstructing circuitry 75 generates tomographic image data of a predetermined number of slices. The image reconstructing circuitry 75 outputs a tomographic image based on the generated tomographic image data to the display control circuitry 76. The image reconstructing circuitry 75 stores the projection data transmitted from the data acquiring circuitry 63 and the generated tomographic image data in the tomographic image data storage circuitry 71.

The display control circuitry 76 displays the tomographic image based on the tomographic image data generated by the image reconstructing circuitry 75 on the monitor 20.

The dose management apparatus 80 manages a dose delivered to the subject P as a skin exposure dose (an exposure dose) in the cardiovascular X-ray diagnosis system 10. The dose management apparatus 80 includes operating circuitry 81, output circuitry 82, human body model generating circuitry 83, data generating circuitry 84, and estimating circuitry 100, for example.

The operating circuitry 81 receives various instructions from the operator who manages an exposure dose delivered to the subject P. The operating circuitry 81, for example, receives an instruction to display the exposure dose delivered to the subject from the operator. Specifically, the operating circuitry 81 receives an instruction to display the exposure dose per minute delivered to the subject from the operator. The operating circuitry 81 also receives an instruction to display the total amount of the exposure dose delivered to the subject P in radiography from the operator.

The output circuitry 82 is a monitor, for example, and displays distributions of an exposure dose generated by the data generating circuitry 84.

The human body model generating circuitry 83 generates a human body model of the subject P or a diagnosis target region based on personal information (e.g., a sex, an age, a height, a weight, and a rough system classification) on the subject P received from the operating circuitry 81 and on supplementary information associated with an X-ray image stored in the X-ray image data storage circuitry 52. The human body model generating circuitry 83 may generate a human body model substantially representing the subject P or other targets with an ellipse, a circle, or the like, or a human body model faithfully representing a human body or other targets. The human body model generating circuitry 83 automatically selects a profile closest to the subject P from a plurality of human body tomographic profiles based on body information on the subject P. The human body model generating circuitry 83 uses the selected profile to create a human body model of the whole body.

The data generating circuitry 84 calculates an exposure dose based on the human body model generated by the human body model generating circuitry 83 and the radiography conditions acquired from the X-ray diagnosis apparatus 200. Thus, the data generating circuitry 84 generates distributions of the exposure dose delivered to the subject P. The data generating circuitry 84 calculates an exposure dose for each pixel in the human body model based on the following: the radiography conditions acquired from the X-ray image data acquiring circuitry 55; various information (e.g., SID and an angle between an axis connecting the X-ray tube 42 and the X-ray detector 43 and the body axis of the subject or a certain reference axis) acquired based on the position of the C-arm 41 acquired from the C-arm control circuitry 54, the position of the couch 30, and the position of the X-ray detector 43; and the thickness of the subject P at each position acquired from the generated human body model. Thus, the data generating circuitry 84 generates distributions of the exposure dose.

Figure 2:
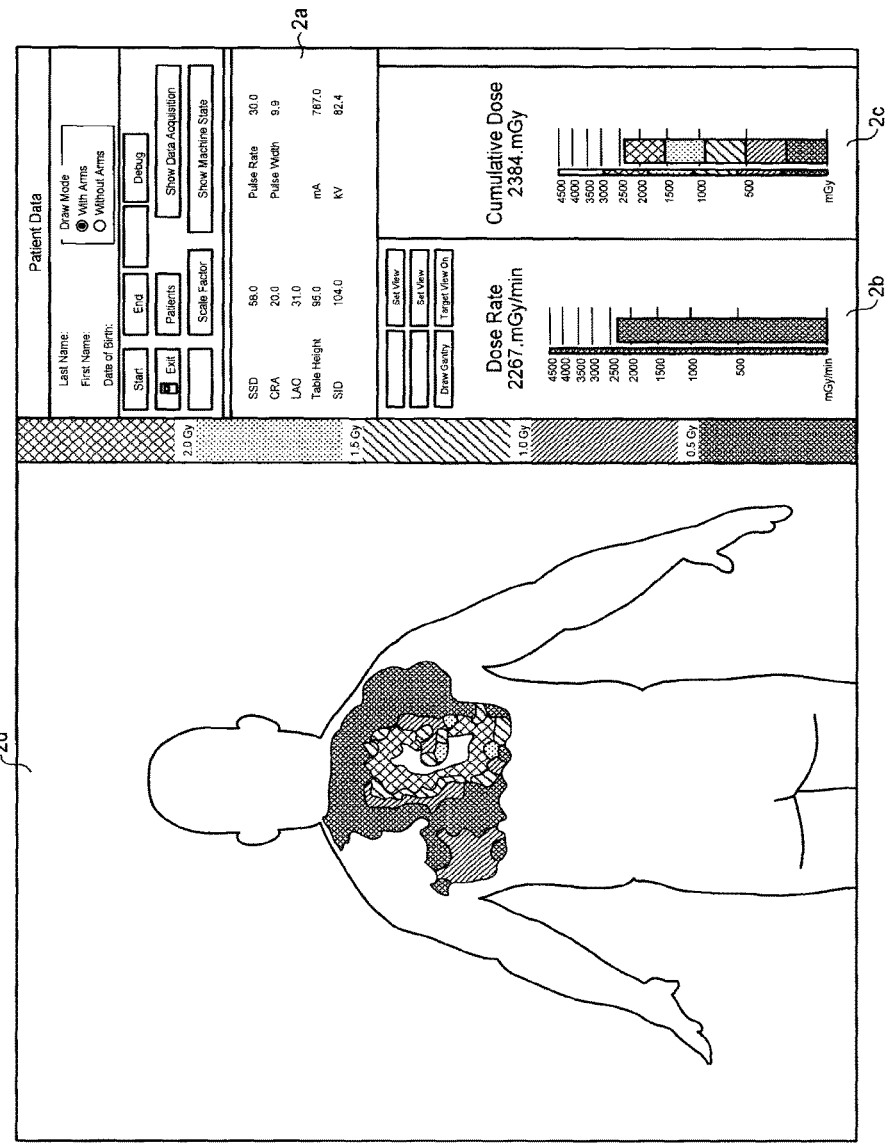
FIG. 2 is a diagram of an example of information managed by a dose management apparatus.

The following describes a screen displayed to manage the exposure dose delivered to the subject P on which radiography is performed by the X-ray diagnosis apparatus 200 with reference to FIG. 2. FIG. 2 illustrates an example of the screen displayed to manage the exposure dose delivered to the subject P on which radiography is performed by the X-ray diagnosis apparatus 200. A screen area 2a in FIG. 2, for example, displays radiography conditions in radiography of X-ray image data performed by the X-ray diagnosis apparatus 200. A screen area 2b in FIG. 2, for example, displays a value of the exposure dose per minute delivered to the subject P in radiography performed by the X-ray diagnosis apparatus 200. A screen area 2c in FIG. 2, for example, displays a value of the total amount (a time integration value) of the exposure dose delivered to the subject P in radiography performed by the X-ray diagnosis apparatus 200.

The dose management apparatus 80 generates information in which the exposure dose is associated with a region on the human body model and displays the information on the monitor 20. Specifically, the dose management apparatus 80 displays, on a screen area 2d illustrated in FIG. 2, image data in which each pixel on the human body model has a color corresponding to the exposure dose.

Figure 3:
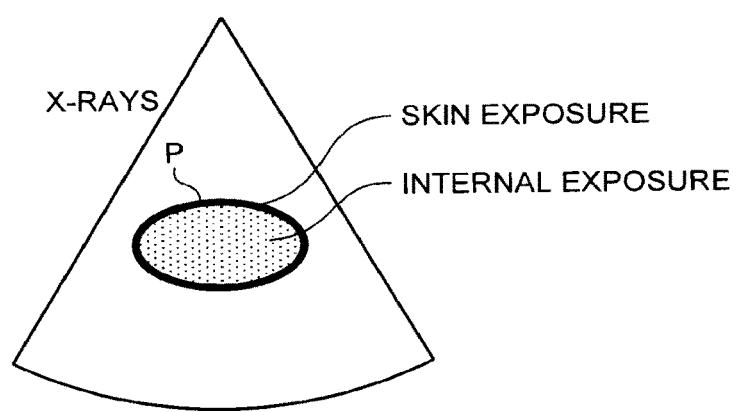
FIG. 3 is a diagram of an internal exposure dose.

In a CT inspection performed by the X-ray CT apparatus 300, the exposure dose delivered to the subject P is calculated as an "internal exposure dose". The following describes the internal exposure dose with reference to FIG. 3. FIG. 3 is a diagram of the internal exposure dose. As illustrated in FIG. 3, the exposure dose measured by the X-ray CT apparatus 300 is calculated as an exposure dose delivered to the inside of the subject P. By contrast, the X-ray diagnosis apparatus 200 manages the exposure dose as a "skin exposure dose", which is an exposure dose delivered to the surface of the subject P. Therefore, the conventional dose management apparatus 80 fails to manage the exposure dose in the CT inspection. To address this, the cardiovascular X-ray diagnosis system 10 according to the first embodiment estimates the skin exposure dose in the CT inspection. Specifically, the estimating circuitry 100 illustrated in FIG. 1 performs estimation of the skin exposure dose in the CT inspection.

The estimating circuitry 100 performs estimation of the skin exposure dose in the CT inspection. The estimating circuitry 100 includes actual measurement value storage circuitry 101, specifying circuitry 102, calculating circuitry 103, and output control circuitry 104, for example.

The actual measurement value storage circuitry 101 stores therein an actual measurement value of an X-ray exposure dose on the surface of a water phantom irradiated with X-rays emitted from the X-ray tube 61 of the X-ray CT apparatus 300 in association with irradiation conditions under which the X-rays are emitted from the X-ray tube 61 of the X-ray CT apparatus 300. The water phantom is used for calibration of the X-ray CT apparatus 300. Typically, a plurality of water phantoms in different sizes are used in calibration. The water phantoms are each designed to have a size of FOV that can be set in radiography performed by the X-ray CT apparatus 300. FOV is set depending on the size of a radiography target in radiography of an X-ray CT image. In the present embodiment, the actual measurement value storage circuitry 101 stores therein actual measurement values of the respective water phantoms in different sizes corresponding to respective FOVs in different sizes used in the X-ray CT apparatus 300. The shape of the water phantoms used in the present embodiment is a regular cylinder, for example. In measurement of the actual measurement value, the water phantoms are arranged such that the central axis of the regular cylinder coincides with the central axis of FOV.

The following describes an example of a data structure stored in the actual measurement value storage circuitry 101 with reference to FIG. 4. FIG. 4 is a diagram of an example of the data structure stored in the actual measurement value storage circuitry 101. As illustrated in FIG. 4, the actual measurement value storage circuitry 101 stores therein information in which "FOV", "kV", "mA", and an "actual measurement value ID" are associated with one another. The "FOV" illustrated in FIG. 4 indicates the size of the water phantom used for the measurement. The "FOV" corresponds to the diameter (unit: mm) of the regular circle of the regular cylinder, for example. The "kV" illustrated in FIG. 4 indicates a tube voltage (unit: kV) supplied to the X-ray tube 61, and the "mA" illustrated in FIG. 4 indicates a tube current (unit: mA) supplied to the X-ray tube 61. The tube voltage and the tube current correspond to irradiation conditions of X-rays in the measurement.

In the present embodiment, actual measurement values are obtained under respective irradiation conditions in each water phantom. The number of irradiation conditions is preferably the number of combinations of the tube voltage and the tube current adjustable by the X-ray CT apparatus 300. The tube voltage typically has three types of values, for example, whereas the value of the tube current can be continuously adjusted. This makes it difficult to estimate the actual measurement value in all combinations. This problem will be described later in greater detail. In a case where the tube current varies depending on the angle of rotation, the actual measurement is performed while taking into consideration the combinations including the variations.

The "actual measurement value ID" illustrated in FIG. 4 indicates an identifier of information indicating the actual measurement value of the X-ray exposure dose on the surface of the water phantom irradiated with X-rays emitted from the X-ray tube 61 of the X-ray CT apparatus 300. Data values, such as "0001-1" and "0002-1", are stored in the "actual measurement value ID", for example.

For example, the actual measurement value storage circuitry 101 illustrated in FIG. 4 indicates that, in a case where "FOV" is "500", "kV" is "220", and "mA" is "I1", the measurement actual value of the X-ray exposure dose on the surface of the water phantom is associated with information identified by "0001-1".

Figure 5:
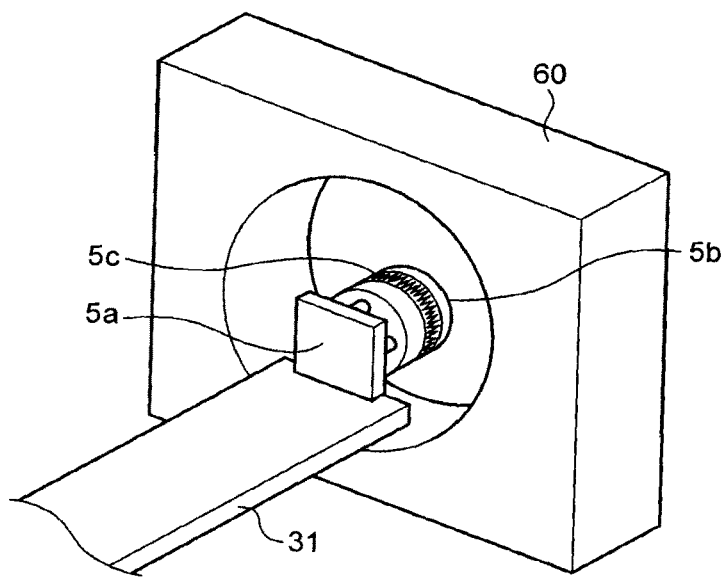
FIG. 5 is a diagram of an example of a method for obtaining an actual measurement value.

The information associated with the actual measurement value ID will be described. The following describes an example of the method for obtaining the actual measurement value with reference to FIG. 5. FIG. 5 is a diagram of an example of the method for obtaining the actual measurement value. FIG. 5 illustrates a case where the couch 30 is moved into the CT apparatus gantry 60 in the X-ray CT apparatus 300. In FIG. 5, a water phantom 5b is fixed to a folder 5a over the couch 30. The water phantom 5b is provided with an X-ray detection sensor 5c. The X-ray detection sensor 5c, for example, records a dose of X-rays emitted under certain irradiation conditions in calibration performed by the X-ray CT apparatus 300. In other words, the dose recorded by the X-ray detection sensor 5c corresponds to an actual measurement value obtained under the certain irradiation conditions.

Figure 6:
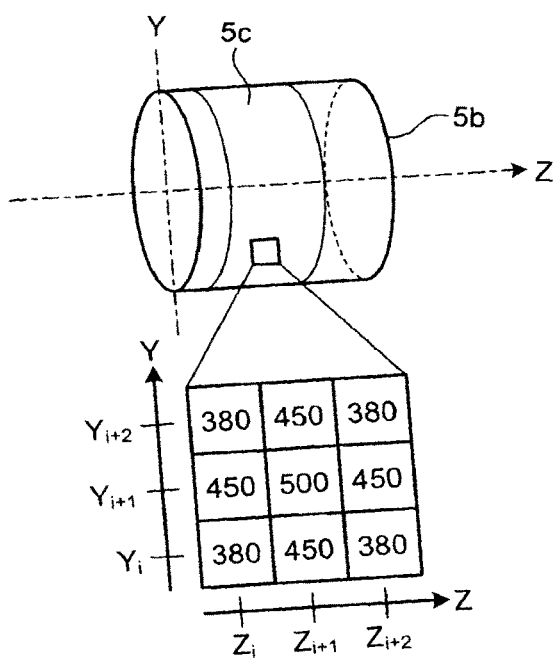
FIG. 6 is a diagram of an example of information associated with an actual measurement value ID.

The following describes an example of information associated with the actual measurement value ID with reference to FIG. 6. FIG. 6 is a diagram of an example of information associated with the actual measurement value ID. FIG. 6 illustrates information the actual measurement value ID of which corresponds to "0001-1". In other words, FIG. 6 illustrates the actual measurement value obtained under the irradiation conditions that "FOV" is "500", "kV" is "220", and "mA" is "I1".

As illustrated in FIG. 6, the X-ray detection sensor 5c provided to the water phantom 5b is divided into a plurality of areas in a predetermined unit and two-dimensionally arranged. In other words, the information associated with the actual measurement value ID is two-dimensionally managed. The position of each area is uniquely specified. FIG. 6 enlarges a part of the X-ray detection sensor 5c provided on the water phantom 5b. As illustrated in FIG. 6, the actual measurement values are obtained in the respective areas resulting from division in the predetermined unit on the surface of the water phantom 5b. In the two-dimensional area illustrated in FIG. 6, for example, the actual measurement value of the dose in the coordinates $(Y_i, Z_i)$ is 380, and the actual measurement value of the dose in the coordinates $(Y_{i+1}, Z_{i+2})$ is 450. In the measurement, a CT scan is performed on the entire periphery of the water phantom to obtain the actual measurement values. The information associated with the actual measurement value ID stores therein the actual measurement values in all the tube phases where the CT scan is performed. The information associated with the actual measurement value ID "0001-1", for example, stores therein the actual measurement values in the respective areas in each tube phase. In other words, the actual measurement values are obtained in each of the tube phases by irradiation of X-rays on the entire periphery of the water phantom.

Referring back to FIG. 1, the specifying circuitry 102 specifies a region of the subject P irradiated with X-rays under the irradiation conditions in radiography performed by the X-ray CT apparatus 300 on the human body model schematically representing the subject P. In other words, the specifying circuitry 102 matches the area on which radiography is performed by the X-ray CT apparatus 300 in the CT inspection with a position on the human body model.

The cardiovascular X-ray diagnosis system 10 provides a reference position in each diagnosis made by the X-ray CT apparatus 300 and the X-ray diagnosis apparatus 200, thereby determining to which position on the couch the created human body model corresponds. The specifying circuitry 102 compares the arrangement position of the center of the detection surface of the C-arm 41 or the X-ray detector 43 with the reference position, thereby associating the created human body model with the couch 30 (or the actual subject P). Alternatively, the specifying circuitry 102 compares movement information on the couchtop 31 included in the supplementary information of the tomographic image data with the reference position, thereby associating the created human body model with the couch (or the actual subject P). The movement information on the couchtop 31 corresponds to positional information on the subject P in radiography performed by the X-ray CT apparatus 300.

The calculating circuitry 103 virtually arranges the human body model at a position where the subject P is arranged in radiography performed by the X-ray CT apparatus 300. Thus, the calculating circuitry 103 acquires an actual measurement value corresponding to the irradiation conditions in the radiography from the actual measurement value storage circuitry 101. The calculating circuitry 103 calculates the X-ray exposure dose on the surface of the region specified by the specifying circuitry 102 on the human body model based on the acquired actual measurement value, the irradiation conditions in the radiography, and the distance from the X-ray tube 61 to the human body model in the radiography.

The calculating circuitry 103, for example, extracts an actual measurement value corresponding to a tube phase in which the X-rays are emitted in radiography from the actual measurement values in each of the tube phases acquired from the actual measurement value storage circuitry 101 as the actual measurement value corresponding to the irradiation conditions in radiography. The calculating circuitry 103 then disperses and projects the extracted actual measurement value onto the surface of the region specified by the specifying circuitry 102 on the human body model, thereby calculating a projection value. The calculating circuitry 103 performs the processing described above in all the tube phases where the X-rays are emitted in the radiography and integrates the projection values of all the tube phases, thereby calculating the exposure dose.

Figure 7:
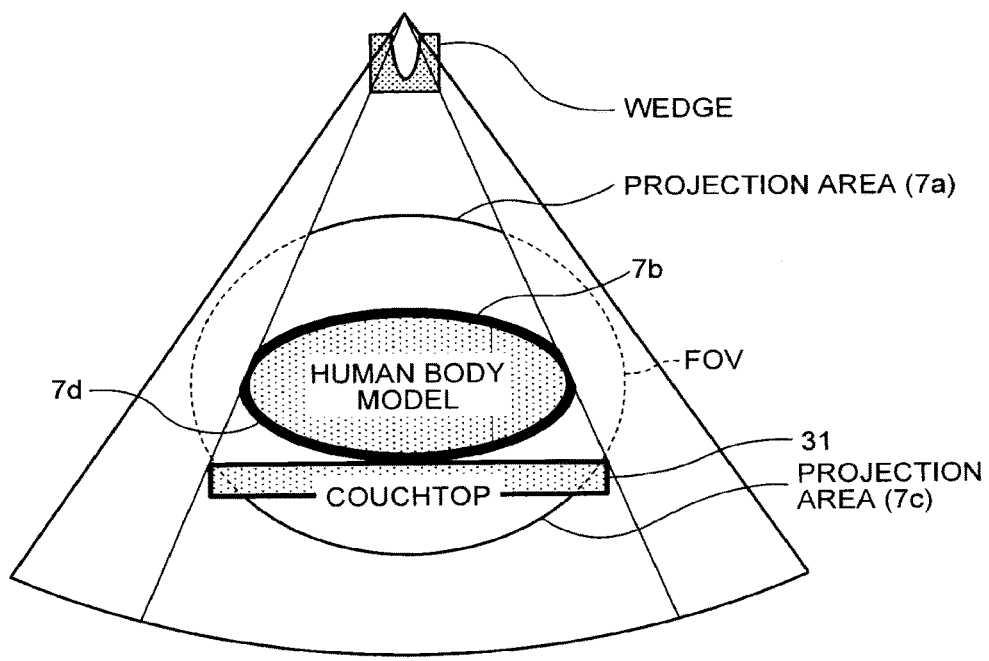
FIG. 7 is a diagram of an example of calculation of an exposure dose performed by calculating circuitry.
Figure 8:
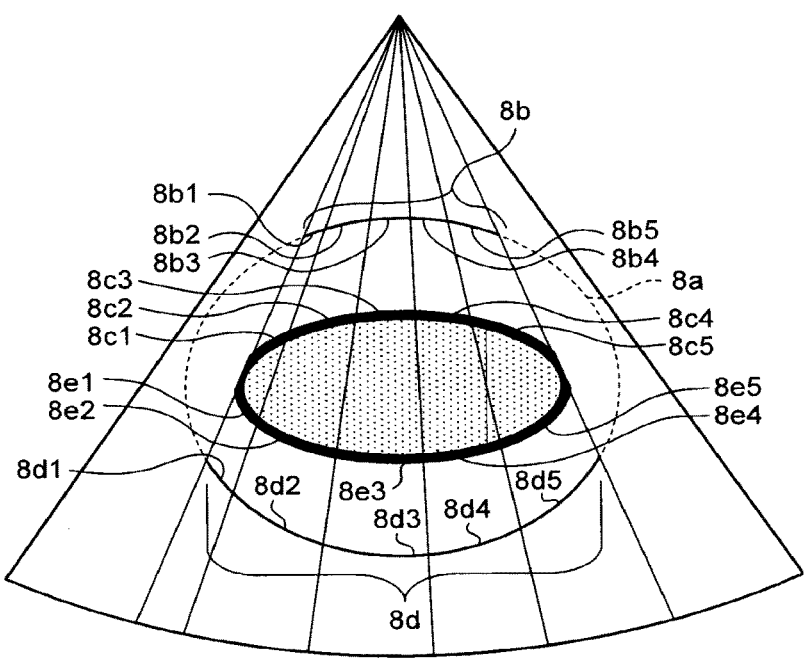
FIG. 8 is a diagram of another example of calculation of an exposure dose performed by the calculating circuitry.

The following describes calculation of the exposure dose performed by the calculating circuitry 103 with reference to FIGS. 7 and 8. While FIGS. 7 and 8 illustrate the water phantom with an ellipse, the actual water phantom is formed in a regular circle. FIG. 7 is a diagram of an example of calculation of the exposure dose performed by the calculating circuitry 103. As illustrated in FIG. 7, the calculating circuitry 103 projects the surface of the water phantom onto the surface of the human body model with the human body model arranged at the center of FOV in the X-ray CT apparatus 300. In the example illustrated in FIG. 7, the water phantom is indicated by the same dashed line as that of FOV. The calculating circuitry 103 projects a projection area 7a indicated by the solid line on the surface of the water phantom onto an area 7b on the surface of the human body model. The calculating circuitry 103 also projects a projection area 7c indicated by the solid line on the surface of the water phantom onto an area 7d on the surface of the human body model. A wedge illustrated in FIG. 7 is a filter used to control an irradiation range of X-rays emitted from the X-ray tube 61 and energy emitted from the X-ray tube 61 and is made of aluminum, for example.

FIG. 8 is a diagram of another example of calculation of the exposure dose performed by the calculating circuitry 103. The calculating circuitry 103 evenly adds the exposure dose on the water phantom to the corresponding area on the human body model in a tube phase. In a case where the actual measurement value storage circuitry 101 stores therein no actual measurement value corresponding to the irradiation conditions in radiography, the calculating circuitry 103 estimates, using an actual measurement value similar to the actual measurement value corresponding to the irradiation conditions, the actual measurement value corresponding to the irradiation conditions, and uses the estimated actual measurement value. In other words, in a case where the value of the tube current is not measured yet when the data is used, the calculating circuitry 103 performs interpolation. In a case where radiography conditions that the tube voltage is "150" and the tube current is "I(m)" are set and where there is no actual measurement value corresponding to the irradiation conditions in radiography, for example, the calculating circuitry 103 performs interpolation using the actual measurement value obtained when the tube voltage is "150" and the tube current is "I(m−1)" and the actual measurement value obtained when the tube voltage is "150" and the tube current is "I(m+1)". Thus, the calculating circuitry 103 estimates the actual measurement value corresponding to the irradiation conditions in radiography. At this time, I(m−1)<I(m)<I(m+1) is satisfied.

In the example illustrated in FIG. 8, the calculating circuitry 103 allocates the actual measurement value of a projection area 8b on the surface of a water phantom 8a indicated by the solid line on the side where the X-ray tube 61 is positioned to the human body model based on the distance from the X-ray tube 61 to the human body model. The following describes a case where the projection area 8b includes areas 8b1 to 8b5. The calculating circuitry 103 projects the area 8b1 onto an area 8c1 on the human body model, thereby calculating a projection value. Let us assume that the exposure dose in the area 8b1 is $\alpha1$ and that the distance from the area 8c1 on the human body model onto which the area 8b1 is projected to the X-ray tube 61 is twice as large as the distance from the area 8b1 on the water phantom to the X-ray tube 61. In this case, the calculating circuitry 103 allocates a dose of $\alpha1/4$ to each pixel in the area 8c1 on the human body model, thereby calculating the projection value. More specifically, while the example illustrated in FIG. 8 indicates the area 8b1 with a line, the area 8b1 is actually a plane. Similarly, the area 8c1 is actually a plane. The total dose incident on the area 8b1 is equal to the total dose incident on the area 8c1. Therefore, the dose per unit area is inversely proportional to the square of the distance from the X-ray tube 61. In other words, if the distance from the X-ray tube 61 increases by twice, the dose per unit area in the area 8c1 decreases by ¼ times. Thus, the calculating circuitry 103 calculates the projection value of the area 8c1 while taking into consideration the sampling area of the area 8b1 on which actual measurement is performed and the size of the pixel area in the area 8c1 on the human body model.

The calculating circuitry 103 allocates the actual measurement value of a projection area 8d on the surface of the water phantom 8a indicated by the solid line on the side where the X-ray detector 62 is positioned to the human body model based on the distance from the X-ray tube 61 to the human body model. The following describes a case where the projection area 8d includes areas 8d1 to 8d5. The calculating circuitry 103 projects the area 8d1 onto an area 8e1 on the human body model, thereby calculating a projection value. Let us assume that the exposure dose in the area 8d1 is $\alpha2$ and that the distance from the area 8e1 on the human body model onto which the area 8d1 is projected to the X-ray tube 61 is ½ times as large as the distance from the area 8d1 on the water phantom to the X-ray tube 61. In this case, the calculating circuitry 103 allocates a dose of $4\times\alpha2$ to each pixel in the area 8e1 on the human body model, thereby calculating the projection value. More specifically, while the example illustrated in FIG. 8 indicates the area 8d1 with a line, the area 8d1 is actually a plane. Similarly, the area 8e1 is actually a plane. The total dose incident on the area 8d1 is equal to the total dose incident on the area 8e1. Therefore, the dose per unit area is inversely proportional to the square of the distance from the X-ray tube 61. In other words, if the distance decreases by ½ times, the dose per circuitry area increases by four times. Thus, the calculating circuitry 103 calculates the projection value of the area 8e1 while taking into consideration the sampling area of the area 8d1 on which actual measurement is performed and the size of the pixel area in the area 8e1 on the human body model. When traveling from the area 8e1 to the area 8d1, the X-rays are attenuated by water between the area 8d1 and the area 8e1. To associate the area 8d1 with the area 8e1, it is necessary to consider the attenuation in the X-rays caused by the water between the area 8d1 and the area 8e1 in a strict sense. In the present embodiment, however, the attenuation in the X-rays caused by the water between the area 8d1 and the area 8e1 can be ignored for the convenience of explanation. By contrast, to associate the area 8b1 with the area 8c1, it is unnecessary to consider the attenuation in the X-rays caused by the water.

In the same manner as described above, the calculating circuitry 103 allocates the exposure dose to each pixel in the areas on the human body model onto which the respective areas 8b2 to 8b5 are projected. In the same manner as described above, the calculating circuitry 103 also allocates the exposure dose to each pixel in the areas on the human body model onto which the respective areas 8d2 to 8d5 are projected. Subsequently, the calculating circuitry 103 integrates the exposure doses in all the tube phases. In other words, the calculating circuitry 103 calculates the projection value of the exposure dose per pixel on the surface of the human body model in each phase. The calculating circuitry 103 then integrates the projection values calculated in each tube phase, thereby calculating the exposure dose. Let us assume that the exposure dose of the projection area 8d on the side where the X-ray detector 62 is positioned can be ignored depending on the irradiation conditions of X-rays. In this case, the calculating circuitry 103 may allocate the actual measurement value of the projection area 8b on the side where the X-ray tube 61 is positioned to the human body model without allocating the actual measurement value of the projection area 8d on the side where the X-ray detector 62 is positioned to the human body model.

In a tube phase where X-rays passing through the couchtop 31 are incident on the subject P on the irradiation path along which the X-rays are emitted in radiography, the calculating circuitry 103 calculates, using an actual measurement value obtained by correcting the exposure dose attenuated relative to the thickness of the couchtop 31, the exposure dose of the X-rays incident on the surface of the region on the human body model. In other words, in a case where the couchtop 31 is present on the irradiation path of the X-rays, the calculating circuitry 103 corrects the actual measurement value to be dispersed and projected depending on the thickness of the couchtop 31.

Figure 9:
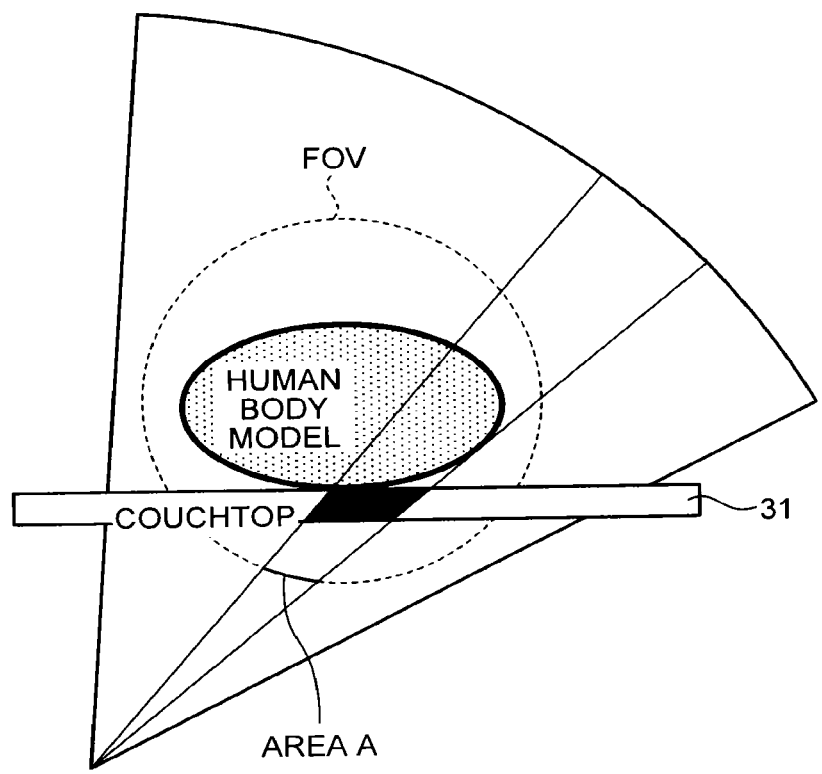
FIG. 9 is a diagram of an example of calculation of an exposure dose performed by the calculating circuitry in a case where a couchtop is present on an irradiation path of X-rays.

The following describes calculation of the exposure dose performed by the calculating circuitry 103 in a case where the couchtop 31 is present on the irradiation path of X-rays with reference to FIG. 9. FIG. 9 is a diagram of an example of calculation of the exposure dose performed by the calculating circuitry 103 in a case where the couchtop 31 is present on the irradiation path of X-rays. As illustrated in FIG. 9, to project an area on the water phantom onto the human body model, the calculating circuitry 103 calculates the volume of the couchtop 31 present on the irradiation path. The calculating circuitry 103 corrects the actual measurement value to be dispersed and projected depending on the attenuation determined based on the calculated volume of the couchtop 31. Let us assume that the exposure dose in an area A on the water phantom is $\alpha 1$, that the distance from the X-ray tube 61 to the human body model onto which the area A is projected is twice as large as the distance from the X-ray tube 61 to the phantom, and that the attenuation is $\alpha x$, for example. In this case, the calculating circuitry 103 allocates a dose of $(\alpha 1 - \alpha x)/4$ to each pixel on the surface of the human body model onto which the area A is projected. In other words, the calculating circuitry 103 calculates the projection value of the area on the human body model while taking into consideration the sampling area of the area A on the water phantom on which actual measurement is performed, the size of the pixel area in the area on the human body model, and the attenuation $\alpha x$ caused by the couchtop 31. In a case where the couchtop 31 is present on the irradiation path of X-rays, the calculating circuitry 103 may calculate the projection value without correcting the exposure dose attenuated relative to the thickness of the couchtop 31 and then correct the calculated projection value depending on the attenuation determined based on the volume of the couchtop 31.

In the description above, actual measurement is performed to obtain data in each phase, and the respective data is used in each tube phase in actual radiography. Alternatively, the present embodiment may perform actual measurement to obtain data in a single tube phase and use the data in a manner rotating it depending on a tube phase. The delivered X-ray dose, however, may possibly not be constant depending on the tube phase. In a case where the variations in the irradiation amount can be ignored, the data in a single tube phase is effectively used. In a case where the variations in the irradiation amount depending on the tube phase cannot be ignored, however, actual measurement is preferably performed to obtain data in all the tube phases of 360 degrees.

Referring back to FIG. 1, the output control circuitry 104 outputs the information in which the exposure dose calculated by the calculating circuitry 103 is associated with the region on the human body model specified by the specifying circuitry 102 to the output circuitry 82. The output control circuitry 104, for example, outputs information in which the calculated exposure dose is associated with the region on the human body model to the output circuitry 82. The exposure dose corresponds to a skin exposure dose. Thus, the dose management apparatus 80 outputs the information in which the exposure dose of X-rays incident on the subject P is associated with the region on the human body model to the output circuitry 82 in radiography performed by the X-ray CT apparatus 300. In other words, the dose management apparatus 80 can output the information in which the exposure dose delivered to the subject P is associated with the region on the human body model to the output circuitry 82 in radiography performed by the X-ray CT apparatus 300 similarly in radiography performed by the X-ray diagnosis apparatus 200 illustrated in FIG. 2.

The output control circuitry 104 may output the information in which the calculated exposure dose is associated with the region on the human body model to an external apparatus via an interface, which is not illustrated. The external apparatus may be the monitor 20, a printer, or a storage medium, for example. Thus, the output control circuitry 104 can transmit the information in which the calculated exposure dose is associated with the region on the human body model to the external apparatus in a reproducible manner.

Figure 10:
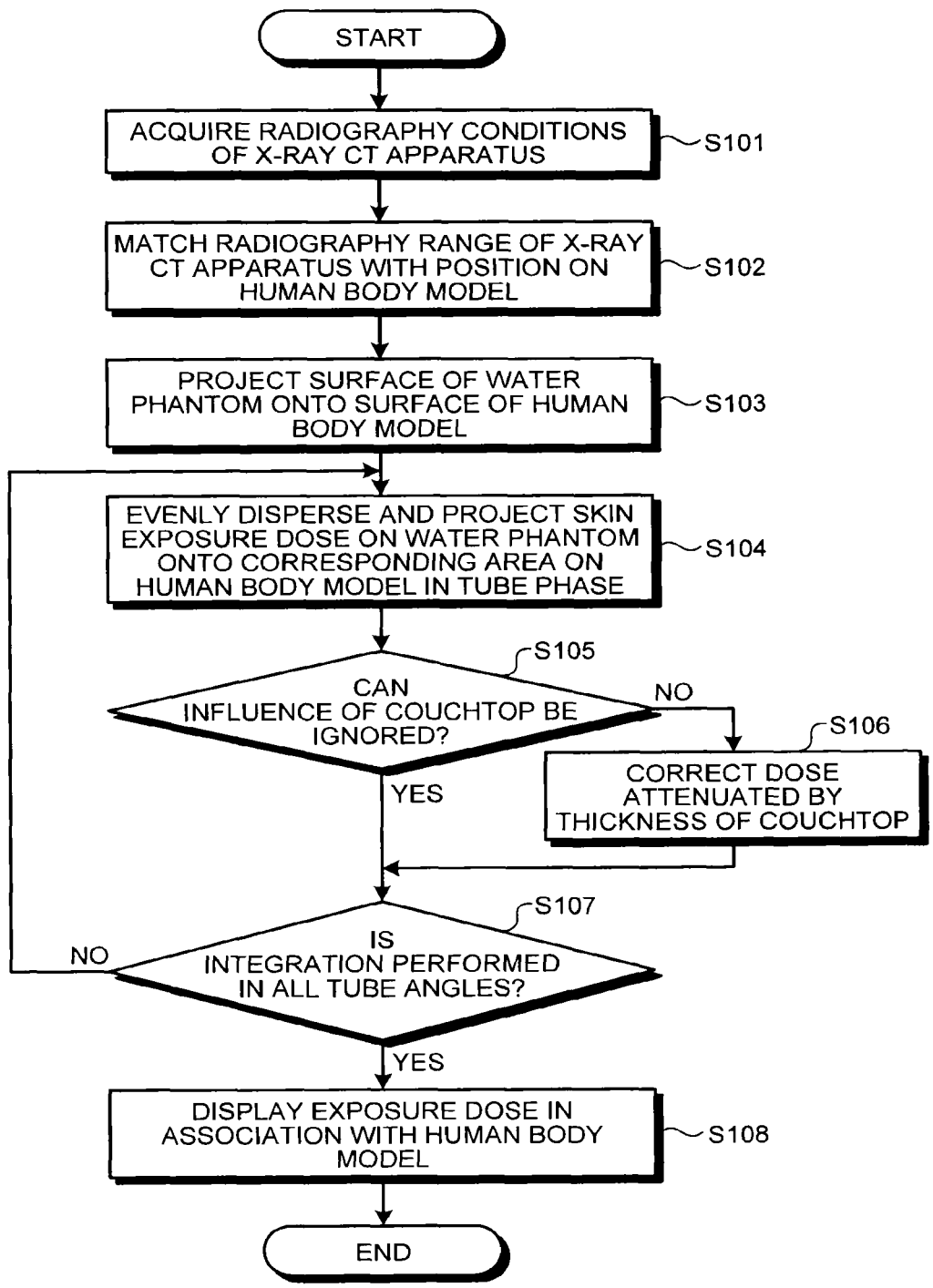
FIG. 10 is a flowchart of a processing procedure performed by an estimating apparatus according to the first embodiment.

The following describes a processing procedure performed by the estimating circuitry 100 according to the first embodiment with reference to FIG. 10. FIG. 10 is a flowchart of a processing procedure performed by the estimating circuitry 100 according to the first embodiment. As illustrated in FIG. 10, the estimating circuitry 100 according to the first embodiment acquires the radiography conditions of the X-ray CT apparatus 300 (Step S101). The estimating circuitry 100, for example, acquires kV, mA, and FOV from the X-ray CT apparatus 300 as the radiography conditions.

Subsequently, the estimating circuitry 100 matches the radiography range of the X-ray CT apparatus 300 with a position on the human body model (Step S102). The estimating circuitry 100, for example, compares the positional information on the subject P in the radiography performed by the X-ray CT apparatus 300 with the reference position, thereby associating the created human body model with the couch 30 (or the actual subject).

The estimating circuitry 100 projects the surface of the water phantom onto the surface of the human body model (Step S103). The estimating circuitry 100, for example, projects the surface of the water phantom onto the surface of the human body model with the human body model arranged at the center of FOV in the X-ray CT apparatus 300. The estimating circuitry 100 evenly disperses and projects the exposure dose on the water phantom onto the corresponding area on the human body model in a tube phase (Step S104).

The estimating circuitry 100 determines whether the influence of the couchtop 31 can be ignored (Step S105). If the estimating circuitry 100 does not determine that the influence of the couchtop 31 can be ignored (No at Step S105), the estimating circuitry 100 corrects the dose attenuated relative to the thickness of the couchtop 31 (Step S106). If the estimating circuitry 100 determines that the influence of the couchtop 31 can be ignored (Yes at Step S105) or if the processing at Step S106 is performed, the estimating circuitry 100 performs the processing at Step S107.

The estimating circuitry 100 determines whether integration is performed in all the tube phases (Step S107). If the estimating circuitry 100 does not determine that integration is performed in all the tube phases (No at Step S107), the estimating circuitry 100 performs the processing at Step S104 and evenly adds the exposure dose on the water phantom to the corresponding area on the human body model in a tube phase. By contrast, if the estimating circuitry 100 determines that integration is performed in all the tube phases (Yes at Step S107), the estimating circuitry 100 displays the exposure dose in association with the human body model (Step S108). If the processing at Step S108 is performed, the estimating circuitry 100 terminates the processing.

As described above, the first embodiment can unitarily manage the exposure dose delivered by the X-ray diagnosis apparatus and the exposure dose delivered by the X-ray CT apparatus. In other words, the first embodiment can estimate and manage the skin exposure dose in the CT inspection, which cannot be managed in the conventional technology. Thus, it is possible to unitarily manage the exposure doses in the CT inspection and the X-ray diagnosis apparatus, thereby reducing the exposure delivered to an examinee.

Modification of Calculation of the Exposure Dose

Figure 11:
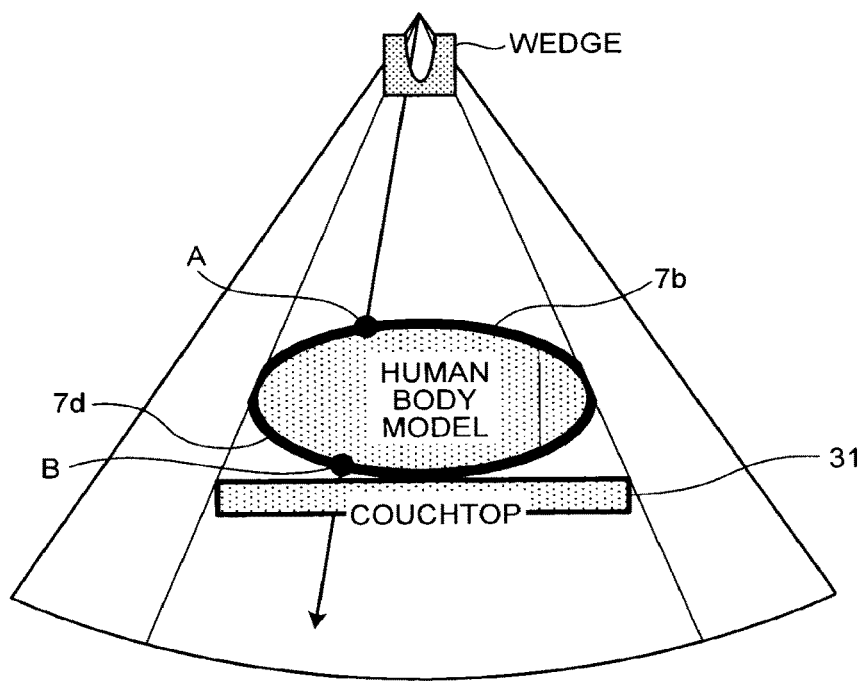
FIG. 11 is a diagram for explaining a modification of the first embodiment.

In the embodiment above, the calculating circuitry 103 calculates the exposure dose using the actual measurement value of the exposure dose on the surface of the phantom. The present embodiment, however, is not limited thereto. The calculating circuitry 103, for example, may calculate the exposure dose not based on the actual measurement value of the exposure dose on the surface of the phantom but on the attenuation rate of X-rays. FIG. 11 is a diagram for explaining a modification of the first embodiment.

The following describes a case where the exposure dose at a body surface point A and a body surface point B is calculated based on the X-ray attenuation rate with reference to FIG. 11. The X-rays emitted from the X-ray tube 61 are attenuated by the wedge before the X-rays reach the body surface point A illustrated in FIG. 11. In a case where the calculating circuitry 103 holds the X-ray attenuation rate of the wedge in advance, for example, the calculating circuitry 103 can calculate the X-ray intensity at the body surface point A using the X-ray attenuation rate of the wedge. For the convenience of explanation of the example illustrated in FIG. 11, let us assume that attenuation in the X-rays in air can be ignored and that the X-rays have only a single energy component. In the example illustrated in FIG. 11, the material of the wedge is aluminum, for example, and the calculating circuitry 103 holds the X-ray attenuation rate per unit length of aluminum. The path-length in the wedge through which the X-rays pass is determined in advance based on the shape of the wedge. The estimating circuitry 100 further includes a storage circuitry that stores therein the intensity of X-rays and the skin exposure dose in a manner associated with each other.

The calculating circuitry 103 calculates the X-ray intensity attenuated by passing through the wedge based on the X-ray attenuation rate per unit length of the wedge and the path-length in the wedge through which the X-rays pass. The calculating circuitry 103 calculates the intensity of X-rays that reach the body surface point A based on the intensity of X-rays determined from the irradiation conditions in radiography and the intensity of X-rays attenuated by passing through the wedge. The calculating circuitry 103 refers to the storage circuitry included in the estimating circuitry 100, thereby calculating the skin exposure dose at the body surface point A from the intensity of X-rays that reach the body surface point A. The calculating circuitry 103 calculates the skin exposure dose at the body surface point A by considering that the intensity of X-rays per unit area is inversely proportional to the square of the distance from the X-ray tube (X-ray source).

The X-rays emitted from the X-ray tube 61 are attenuated by the wedge and the inside of the subject before the X-rays reach the body surface point B illustrated in FIG. 11. In a case where the calculating circuitry 103 holds the X-ray attenuation rate of the wedge and the X-ray attenuation rate of the human body model in advance, for example, the calculating circuitry 103 can calculate the X-ray intensity at the body surface point B using the X-ray attenuation rate of the wedge and the X-ray attenuation rate of the human body model.

More specifically, the calculating circuitry 103 calculates the X-ray intensity attenuated by passing through the wedge based on the X-ray attenuation rate per unit length of the wedge and the path-length in the wedge through which the X-rays pass. The calculating circuitry 103 calculates the intensity of X-rays attenuated by passing through the human body model based on the X-ray attenuation rate per unit length of the human body model and the path-length of the human body model (length between the body surface point A and the body surface point B). The calculating circuitry 103 calculates the intensity of X-rays that reach the body surface point B based on the intensity of X-rays determined from the irradiation conditions in radiography, the intensity of X-rays attenuated by passing through the wedge, and the intensity of X-rays attenuated by passing through the human body model. The calculating circuitry 103 refers to the storage circuitry included in the estimating circuitry 100, thereby calculating the skin exposure dose at the body surface point B from the intensity of X-rays that reach the body surface point B. The calculating circuitry 103 calculates the skin exposure dose at the body surface point B by considering that the intensity of X-rays per unit area is inversely proportional to the square of the distance from the X-ray tube (X-ray source).

In a case where the X-rays include components in a plurality of energy bands, performing the calculation for each energy band makes it possible to estimate the skin exposure dose at each body surface. In a case where the exposure dose at the body surface point B can be ignored, the calculating circuitry 103 may calculate the exposure dose only at the body surface point A.

The X-ray attenuation rate of the wedge and the path-length in the wedge through which the X-rays pass can be determined in advance based on the shape of the wedge of the X-ray CT apparatus 300. Thus, the estimating circuitry 100 may store the intensity of X-rays emitted from the X-ray tube of the X-ray CT apparatus 300, the skin exposure dose at the body surface point A, and the skin exposure dose at the body surface point B in the storage circuitry in a manner associated with one another for each type of the human body model based on the shape of the wedge of the X-ray CT apparatus 300. In this case, the calculating circuitry 103 derives the X-ray exposure dose at the body surface point A specified on the human body model based on the irradiation conditions in radiography performed by the X-ray CT apparatus 300. The calculating circuitry 103, for example, specifies the intensity of X-rays determined from the irradiation conditions in radiography. The calculating circuitry 103 refers to the storage circuitry included in the estimating circuitry 100, thereby deriving the skin exposure dose at the body surface point A associated with the specified intensity of X-rays. Furthermore, the calculating circuitry 103 refers to the storage circuitry included in the estimating circuitry 100, thereby deriving the skin exposure dose at the body surface point B associated with the specified intensity of X-rays. The calculating circuitry 103 may also be referred to as a "deriving circuitry".

Figure 12:
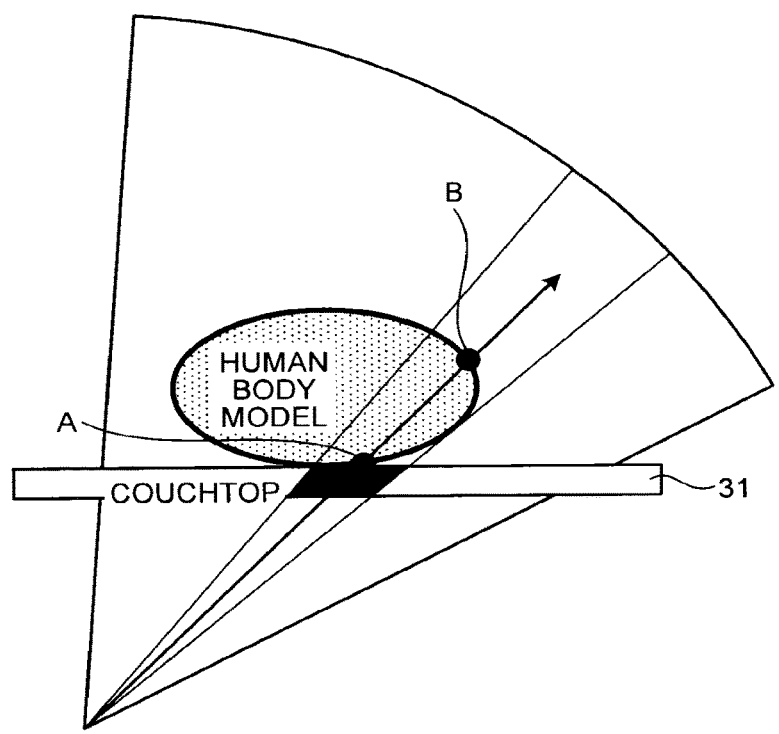
FIG. 12 is a diagram for explaining another modification of the first embodiment.

In the example illustrated in FIG. 11, the influence of the couchtop is ignored. If there is no practical inconvenience, the calculating circuitry 103 may calculate the skin exposure dose, ignoring the influence of the couchtop. By contrast, if attenuation caused by the couchtop cannot be ignored, the calculating circuitry 103 takes into consideration the X-ray attenuation caused by the couchtop and performs calculation similar to that of the skin exposure dose at the body surface point A and the body surface point B described with reference to FIG. 11. FIG. 12 is a diagram for explaining another modification of the first embodiment.

The transmission path-length of each X-ray beam in the couchtop at each tube angle can be derived by calculation, for example. In a case where the material of the couchtop is assumed to be uniform and where the X-ray attenuation rate per unit length is specified, the calculating circuitry 103 calculates the skin exposure dose at the body surface point A and the skin exposure dose at the body surface point B while taking into consideration the X-ray attenuation caused by the couchtop.

Modification of the X-Ray Diagnosis Apparatus

In the embodiment above, the dose management apparatus 80 outputs information (hereinafter, referred to as "first skin exposure information") in which the skin exposure dose of X-rays incident on the subject P is associated with a region on the human body model to the output circuitry 82 in radiography performed by the X-ray CT apparatus 300. In the embodiment above, the dose management apparatus 80 outputs information (hereinafter, referred to as "second skin exposure information") in which the skin exposure dose of X-rays incident on the subject P is associated with a region on the human body model to the output circuitry 82 in radiography performed by the X-ray diagnoses apparatus 200. The embodiment, however, is not limited thereto. Intravascular treatment, for example, is sometimes performed in a manner supported by the X-ray diagnosis apparatus 200 after a diagnosis is made by the X-ray CT apparatus 300. Thus, the display control circuitry 56 of the X-ray diagnosis apparatus 200 may display the first skin exposure information and the second skin exposure information on a predetermined display, such as the monitor 20.

In this case, the X-ray diagnosis system control apparatus 50 acquires the first skin exposure information and the second skin exposure information from the dose management apparatus 80. The display control circuitry 56 displays the acquired first skin exposure information and second skin exposure information on the monitor 20. The display control circuitry 56 divides the display area on the monitor 20, displays the first skin exposure information on one of the display areas, and displays the second skin exposure information on the other.

Alternatively, the display control circuitry 56 may display the first skin exposure information and the second skin exposure information without dividing the display area on the monitor 20. In this case, the display control circuitry 56 integrates the skin exposure dose indicated by the first skin exposure information and the skin exposure dose indicated by the second skin exposure information for each region on the human body model, for example. The display control circuitry 56 displays the integrated value of the skin exposure dose resulting from integration for each region in a manner associated with a region on the human body model.

The X-ray image data acquiring circuitry 55 may control the C-arm control circuitry 54 to move and rotate the C-arm 41 based on at least one of the first skin exposure information and the second skin exposure information. In this case, the X-ray diagnosis apparatus 200 may further include a setting circuitry that sets a certain threshold for the exposure dose on the surface of the subject. The X-ray image data acquiring circuitry 55 moves and rotates the C-arm 41 when the exposure dose on the surface of the subject based on at least one of the first skin exposure information and the second skin exposure information exceeds the threshold.

More specifically, the X-ray image data acquiring circuitry 55 moves and rotates the C-arm 41 when the integrated value of the skin exposure dose on a certain region on the human body model exceeds the certain threshold. Alternatively, the X-ray image data acquiring circuitry 55 moves and rotates the C-arm 41 when the skin exposure dose indicated by the second skin exposure information on a certain region on the human body model exceeds the certain threshold. This mechanism can prevent a certain region of the subject from having a high exposure dose when a CT inspection with the X-ray CT apparatus is performed in combination with treatment with the X-ray diagnosis apparatus. The X-ray diagnosis apparatus 200 may receive a setting of the certain threshold from the operator. The X-ray image data acquiring circuitry 55 may stop irradiation of the subject with X-rays when the exposure dose on the surface of the subject based on at least one of the first skin exposure information and the second skin exposure information exceeds the threshold.

The components illustrated in the drawings are functionally conceptual and are not necessarily physically configured as illustrated. The X-ray diagnosis apparatus 200 and the dose management apparatus 80 may be integrated as an X-ray diagnosis apparatus, for example. In this case, the X-ray diagnosis apparatus can receive radiography conditions and image data resulting from radiography from an external X-ray CT apparatus connected via a network, such as a local area network (LAN). With this configuration, the X-ray diagnosis apparatus can manage not only the exposure dose acquired from the X-ray CT apparatus 300 but also the exposure dose obtained when the same subject P is inspected with another X-ray CT apparatus.

The functions included in the estimating circuitry 100 may be independently provided as an estimating apparatus. In this case, the estimating apparatus can receive radiography conditions and image data resulting from radiography from an external apparatus (e.g., an X-ray diagnosis apparatus, an X-ray CT apparatus, and an image server) connected via a network, such as a LAN. With this configuration, the estimating apparatus can manage not only the exposure dose acquired from the X-ray diagnosis apparatus 200 and the X-ray CT apparatus 300 but also the exposure dose obtained when the same subject P is inspected with another X-ray diagnosis apparatus or another X-ray CT apparatus.

The X-ray diagnosis apparatus 200 may include the human body model generating circuitry 83 and the data generating circuitry 84, which is included in the dose management apparatus 80 in the drawings, and the X-ray CT apparatus 300 may include the estimating circuitry 100, which is included in the dose management apparatus 80 in the drawings.

All or an arbitrary part of the processing functions performed by each apparatus can be provided by a central processing unit (CPU) and a computer program analyzed and excused by the CPU or provided as hardware by wired logic.

As described above, the first embodiment can unitarily manage the exposure dose delivered by the X-ray diagnosis apparatus and the exposure dose delivered by the X-ray CT apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An estimating apparatus, comprising:
a memory storing a value of an exposure dose on a surface irradiated with X-rays emitted from an X-ray tube of an X-ray CT apparatus in association with irradiation conditions under which the X-rays are emitted from the X-ray tube of the X-ray CT apparatus;
specifying circuitry configured to specify a region of a subject irradiated with the X-rays emitted from the X-ray tube of the X-ray CT apparatus on a human body model schematically representing the subject;
deriving circuitry configured to assume the human body model to be at a position where the subject is arranged in radiography performed by the X-ray CT apparatus and derive, as a skin exposure dose, an exposure dose of the X-rays on a surface of the region specified by the specifying circuitry on the human body model based on the value corresponding to certain irradiation conditions used in the radiography, the value being acquired from the memory, and the certain irradiation conditions used in the radiography; and
display control circuitry configured to display, on a display, information in which the skin exposure dose derived by the deriving circuitry is associated with the region on the human body model specified by the specifying circuitry.

2. The estimating apparatus according to claim 1, wherein the deriving circuitry is further configured to derive the exposure dose of the X-rays on the surface of the region specified by the specifying circuitry on the human body model based on the certain irradiation conditions used in the radiography and a distance from the X-ray tube to the human body model in the radiography.

3. The estimating apparatus according to claim 1, wherein
the memory further stores, as the value, an actual measurement value of the exposure dose on a surface of a phantom irradiated with the X-rays emitted from the X-ray tube of the X-ray CT apparatus in association with the certain irradiation conditions under which the X-rays are emitted from the X-ray tube of the X-ray CT apparatus, and
the deriving circuitry is further configured to derive the exposure dose of the X-rays on the surface of the region specified by the specifying circuitry on the human body model based on an actual measurement value corresponding to the certain irradiation conditions used in the radiography, the actual measurement value being acquired from the memory, the certain irradiation conditions in the radiography, and the distance from the X-ray tube to the human body model in the radiography.

4. The estimating apparatus according to claim 3, wherein the actual measurement value is obtained in each of a plurality of tube phases by irradiation of the X-rays on the entire periphery of the phantom, and
the deriving circuitry is further configured to perform calculation of a projection value by dispersing and projecting an actual measurement value corresponding to a tube phase in which the X-rays are emitted in the radiography out of the actual measurement value in each of the tube phases acquired from the memory as the actual measurement value corresponding to the certain irradiation conditions used in the radiography onto the surface of the region specified by the specifying circuitry on the human body model in all tube phases where the X-rays are emitted in the radiography and integrates the projection value of all tube phases, thereby calculating the exposure dose.

5. The estimating apparatus according to claim 3, wherein, when no actual measurement value corresponding to the certain irradiation conditions used in the radiography is stored in the memory, the deriving circuitry is further configured to estimate, using an actual measurement value similar to the actual measurement value corresponding to the certain irradiation conditions, the actual measurement value corresponding to the certain irradiation conditions, and uses the estimated actual measurement value.

6. The estimating apparatus according to claim 3, wherein, in a tube phase where the X-rays passing through a couchtop are incident on the subject on an irradiation path along which the X-rays are emitted in the radiography, the deriving circuitry is configured to calculate, using the actual measurement value obtained by correcting the exposure dose attenuated relative to the thickness of the couchtop, the exposure dose of the X-rays incident on the surface of the region on the human body model.

7. The estimating apparatus according to claim 1, wherein
the memory further stores an intensity of the X-rays and the exposure dose in a manner associated with each other, and
the deriving circuitry is further configured to calculate the intensity of the X-rays that reach the surface of the region specified by the specifying circuitry based on the intensity of the X-rays determined from the certain irradiation conditions used in the radiography and the intensity of the X-rays attenuated before the X-rays reach the surface of the specified region and derive the exposure dose associated with the calculated intensity of the X-rays as the exposure dose on the surface of the specified region.

8. The estimating apparatus according to claim 7, wherein, in a tube phase where the X-rays passing through a couchtop are incident on the subject on an irradiation path along which the X-rays are emitted in the radiography, the deriving circuitry is further configured to calculate, using the intensity of the X-rays obtained by correcting the intensity of the X-rays attenuated relative to the thickness of the couchtop, the exposure dose of the X-rays incident on the surface of the region on the human body model.

9. The estimating apparatus according to claim 7, wherein the deriving circuitry is further configured to calculate the intensity of the attenuated X-rays based on an attenuation rate of an object that attenuates the X-rays and a distance in the object through which the X-rays pass before the X-rays reach the surface of the specified region.

10. An X-ray diagnosis apparatus, comprising:
a memory storing a value of an exposure dose on a surface irradiated with X-rays emitted from an X-ray tube of an X-ray CT apparatus in association with irradiation conditions under which the X-rays are emitted from the X-ray tube of the X-ray CT apparatus;

data acquiring circuitry configured to rotate an arm holding an X-ray source that generates the X-rays and an X-ray detector that detects the X-rays emitted from the X-ray source, irradiate a subject with the X-rays emitted from the X-ray source under certain irradiation conditions, and acquire data of the X-rays detected by the X-ray detector;

specifying circuitry configured to specify a region of a subject irradiated with the X-rays emitted from the X-ray tube of the X-ray CT apparatus on a human body model schematically representing the subject;

deriving circuitry configured to assume a human body model to be at a position where the subject is arranged in radiography performed by the X-ray CT apparatus and derive first skin exposure information in which an exposure dose of the X-rays on a surface of the region specified by the specifying circuitry on the human body model based on the value corresponding to the certain irradiation conditions used in the radiography, the value being acquired from the memory, and the irradiation conditions used in the radiography; and display control circuitry configured to display, on a display, the first skin exposure information and second skin exposure information in which an exposure dose on the surface of the subject based on the X-rays emitted from the X-ray source in acquisition of the data is associated with the region on the human body model.

11. The X-ray diagnosis apparatus according to claim 10, wherein the first skin exposure information is obtained based on the exposure dose on a surface of a phantom irradiated with the X-rays emitted from the X-ray tube of the X-ray CT apparatus, the certain irradiation conditions under which the X-rays are emitted from the X-ray tube of the X-ray CT apparatus, and a distance from the X-ray tube to the human body model.

12. The X-ray diagnosis apparatus according to claim 10, wherein the data acquiring circuitry moves the arm based on at least one of the first skin exposure information and the second skin exposure information.

13. The X-ray diagnosis apparatus according to claim 12, further comprising:

setting circuitry configured to set a threshold for the exposure dose on the surface of the subject, wherein the data acquiring circuitry moves the arm when the exposure dose on the surface of the subject based on at least one of the first skin exposure information and the second skin exposure information exceeds the threshold.

14. An estimating method, comprising:

storing, in a memory, a value of an exposure dose on a surface irradiated with X-rays emitted from an X-ray tube of an X-ray CT apparatus in association with irradiation conditions under which the X-rays are emitted from the X-ray tube of the X-ray CT apparatus;

specifying a region of a subject irradiated with the X-rays emitted from the X-ray tube of the X-ray CT apparatus on a human body model schematically representing the subject;

assuming the human body model to be at a position where the subject is arranged in radiography performed by the X-ray CT apparatus, deriving, as a skin exposure dose, an exposure dose of the X-rays on a surface of the specified region on the human body model based on the value corresponding to the irradiation conditions used in the radiography, the value being acquired from the memory, and the certain irradiation conditions used in the radiography; and displaying, on a display, information in which the skin exposure dose derived in the deriving step is associated with the region on the human body model specified in the specifying step.

* * * * *